United States Patent [19]

Weiss et al.

[11] Patent Number: 4,587,337
[45] Date of Patent: May 6, 1986

[54] PROCESS FOR THE PREPARATION OF 2-AMINO-S-TRIAZINES

[75] Inventors: Stefan Weiss; Helmut Krommer, both of Trostberg, Fed. Rep. of Germany

[73] Assignee: SKW Trostberg Aktiengesellschaft, Fed. Rep. of Germany

[21] Appl. No.: 715,114

[22] Filed: Mar. 25, 1985

[30] Foreign Application Priority Data

Mar. 27, 1984 [DE] Fed. Rep. of Germany ....... 3411202
Mar. 27, 1984 [DE] Fed. Rep. of Germany ....... 3411203

[51] Int. Cl.$^4$ ................. C07D 251/16; C07D 251/18; C07D 251/42
[52] U.S. Cl. ..................................... 544/194; 544/205
[58] Field of Search ............................... 544/194, 205

[56] References Cited

U.S. PATENT DOCUMENTS 3,154,547 10/1964 Huffman ............................. 544/194

FOREIGN PATENT DOCUMENTS 1380818 10/1964 France .

OTHER PUBLICATIONS

Huffman et al., *J. Org. Chem.*, pp. 1816–1821, (1963).
Lwowski, *Synthesis*, p. 263 (1971).
Pinner, "Die Imidoether and the Derivate" pp. 26–27, Berlin (1892).

*Primary Examiner*—John M. Ford
*Attorney, Agent, or Firm*—Thomas L. Tully

[57] ABSTRACT

The present invention relates to a process for the preparation of 2-amino-s-triazines in three stages. In the first stage nitriles, alcohols and hydrogen chloride are reacted to form the corresponding imido-ester hydrochlorides. In the second stage, the imido-ester hydrochlorides are reacted with cyanamide in the aqueous phase to form the N-cyanimido-esters, which comprises carrying out the first stage in the presence of acetic acid esters and the second stage in an aqueous solution which has been brought to a pH value of 5–8 by addition of bases, and reacting the N-cyanimido-esters with O-alkylisourea, S-alkylisothiourea, guanidine or amidine salts in the presence of a base in the third stage. The 2-amino-s-triazines can be prepared in a high purity and with good yields in this manner.

28 Claims, No Drawings

PROCESS FOR THE PREPARATION OF 2-AMINO-S-TRIAZINES

BACKGROUND OF THE INVENTION

2-Amino-s-triazines are important products having important utilities as plant protection agents, optical brighteners and as pharmaceutical agents. Synthesis methods starting from cyanuric chloride are known for most of these compounds. However, if s-triazine derivatives with alkyl substituents in the 4- or 6-position are to be prepared, starting substances other than cyanuric chloride must be used.

Thus, the preparation of 2-amino-4-alkyl-6-methoxy (ethoxy)-s-triazines is known from French Pat. No. 1,380,818, the corresponding triazines being formed by a cyclization reaction of guanyl-O-methyl (or ethyl)-isourea with carboxylic acid chlorides or carboxylic acid esters. However, this method is only suitable on a laboratory scale, since the yields are extremely low and the guanyl-O-methyl- and guanyl-O-ethyl-isourea hydrochloride required as starting substances are only accessible with difficulty and are thus unavailable on an industrial scale.

According to U.S. Pat. No. 3,754,547, 2-amino-s-triazine derivatives can be prepared by reaction of N-cyanimido-esters with guanidine, O-methylisourea or amides. This process is also unsuitable on an industrial scale, since the yields produced are only about one-half of the desired yield (a maximum yield of 45% results in the case of the important compound 2-amino-4-methoxy-6-methyl-s-triazine), and the free O-methylisourea base, which is relatively unstable, must be used as the starting substance in this process.

Another preparation route, for example, for 2-amino-4-methoxy-6-methyl-s-triazine, involves the reaction of N-cyanoacetimido-esters with sodium hydrogen cyanamide in methanolic solution, sodium N,N-dicyanoacetamidine being formed as the intermediate (cf. K. R. Huffmann and F. C. Schaefer, J. Org. Chem. 28, page 1816 (1963)). The desired product is then formed in 65% yield by cyclizing the intermediate in the presence of methanol and excess hydrogen chloride. This process is also relatively complicated and therefore too difficult and too expensive for use as an industrial process.

N-Cyanimido-esters of the general formula I are also important synthesis units for the preparation of plant protection agents, pharmaceuticals and other fine and specialized chemicals:

(I)

$R_1$=H, alkyl with 1 to 24 carbon atoms, aralkyl or aryl;
$R_2$=alkyl with 1 to 4 carbon atoms.

Although a two-stage process for the preparation of N-cyanimido-esters has been known for a long time, such process was suitable only for use on a laboratory scale. In the first stage, to prepare the imido-ester hydrochlorides, hydrogen chloride was usually passed into a equimolar mixture of alcohol and nitrile and the mixture was left to stand for a prolonged period, the reaction mixture solidifying as the reaction progressed (cf. A. Pinner "Die Imidoather and ihre Derivate" ("The imido-ethers and their derivatives") Berlin 1892).

This reaction is difficult to carry out in industry as in the use of diethyl ether and dioxane as diluents. According to U.S. Pat. No. 3,402,193, the preparation of butyramidine hydrochloride is described, using an excess of butyronitrile. However, the butyrimido-ethyl ester hydrochloride which is probably formed as an intermediate is not isolated and identified. In the preparation of butyramidine hydrochloride in the presence of butyl acetate, according to U.S. Pat. No. 3,538,139, there is also no isolation and identification of the butyrimido-ethyl ester hydrochloride which is probably formed as an intermediate. The yield of butyramidine hydrochloride is only 33%, and 45% of the unreacted butyronitrile is recovered. None of these known processes for the preparation of imido-ester hydrochlorides can be used industrially, either because the yields are too low or because of the cumbersome preparation methods.

Also, for the second stage, i.e., the preparation of N-cyanimido-esters from the imido-ester hydrochlorides and cyanamide, no processes are known which appear to be industrially useful both with respect to the yields and with respect to the byproducts obtained. Thus, for example, according to U.S. Pat. No. 3,225,077, the preparation of N-cyanimido-esters by the action of solid, anhydrous cyanamide on the corresponding acetimido-ester hydrochloride in alcoholic solution is described. Aside from the relatively low yields of not more than 66%, this synthesis route is relatively expensive and thus uneconomical, because solid, anhydrous cyanamide must be used as the starting substance.

The preparation of N-cyanoacetimido-ethyl ester hydrochloride in aqueous solution is therefore a preparative advance (cf. W. Lwowski, Synthesis 1971, page 263), the reaction being carried out in the presence of stoichiometric amounts of disodium hydrogen phosphate. The decisive disadvantages of this procedure are the low yield of 58%, based on the acetimido-ester hydrochloride, the release of ammonia and the formation of sodium chloride and sodium dihydrogen phosphate as byproducts.

SUMMARY OF THE INVENTION

The present invention is concerned with providing a process for the preparation of 2-amino-s-triazines in three stages, the first stage involving reacting nitriles, alcohols and hydrogen chloride to form the corresponding imido-ester hydrochlorides, and the second stage involving the subsequent reaction of the formed imido-ester hydrochlorides with cyanamide in an aqueous medium to form the N-cyanimido-esters, which process does not have the disadvantages mentioned for the prior art, and allows preparation of these products in high yields in an industrially simple manner.

According to the invention, this is achieved by carrying out the first stage in the presence of acetic acid esters and the second stage in an aqueous solution which has been brought to a pH value of 5-8 by addition of bases, and then reacting the formed N-cyanimido-esters in a third stage with O-alkylisourea, S-alkylisothiourea, guanidine or amidine salts in the presence of a base.

Surprisingly, it has been found that, with the aid of the process according to the invention, 2-amino-s-triazines can be obtained in a very simple manner over all three stages and with very high yields and in good purities.

The first stage of the process according to the invention is carried out, for example, by a procedure in which a solution of the alcohol, the corresponding nitrile and the acetic acid ester is prepared and the hydrogen chloride is passed into this solution, during which moisture should be excluded, as far as possible. The alcohol and the nitrile can be employed in exactly or approximately equimolar amounts, and the hydrogen chloride should be introduced in an amount such that the molar ratio of nitrile: hydrogen chloride is 1:1 to 1:1.2. Although in principle it is possible to use a larger excess of HCl, this can lead to increased corrosion problems on an industrial scale. From 0.3-2 moles of acetic acid ester, preferably 0.5-1 mole, should be employed per mole of nitrile, if the reuse of the filtrates as a diluent and reaction medium is dispensed with. Larger amounts of acetic acid ester can be used, but generally this is not necessary.

Suitable acetic acid esters are, in particular, methyl, ethyl, propyl and butyl acetate. In order to prevent possible transesterification reactions, it is preferred to choose the solvent which has the same ester grouping as the desired imido-ester, for example, methyl acetate is used for the preparation of imido-methyl ester hydrochlorides.

Preferred nitriles are hydrocyanic acid, aliphatic nitriles with an alkyl radical of 1 to 24 carbon atoms and nitriles with an aralkyl radical, such as benzyl, or an aromatic radical, such as phenyl.

Examples of alcohols which can be used in the first stage are aliphatic alcohols with a branched or straight-chain alkyl radical of 1 to 4 carbon atoms.

The temperature of the first reaction stage can be varied between $-10°$ and $+45°$ C., the temperature range between $10°$ and $30°$ C. being preferred. If the temperature is too high, undesirable side reactions may occur, such as formation of ortho-esters and amides.

A preferred embodiment of the present invention comprises passing hydrogen chloride into a mixture of alcohol and nitrile in the first reaction stage, and then leaving the mixture to react, in the absence of the acetic acid ester, until the reaction mixture becomes more difficult to stir. Only then is the acetic acid ester added, in portions, in a manner such that the reaction mixture can always still just be stirred, which of course depends on the technical nature of the stirring device. When the reaction has ceased, further acetic acid ester must be added, if further thickening is required, so that the reaction mixture can be reactivated.

The imido-ester hydrochlorides, which are obtained in high yields of 93-95% and in high purity, are isolated by known methods, such as by cooling or concentrating the solution and subsequently separating off the solids.

In another preferred embodiment, it is also possible for the mother filtrate or centrifugate, obtained after the imido-ester hydrochloride has been separated off, to be reused as the diluent and/or reaction medium for the next batch without treatment of the filtrate or centrifugate, for example by distillative separation, being necessary. By this recycling and reusing of the filtrates, which surprisingly leads to little or no substantial reduction in the product quality, the reaction times can be shortened and the required amounts of acetic acid esters greatly reduced. Thus, for example, if the filtrate is used five times in the preparation of the acetimido-ethyl ester hydrochloride, only about 120 to 150 g of ethyl acetate are required for 1 kg of product.

Because of the simple procedure, it is possible to carry out the first reaction stage either batchwise, semicontinuously or continuously. In the continuous procedure, for example, the filtrate and centrifugate can be circulated and replaced gradually with fresh acetic acid ester, while the spent solvent is continuously discharged.

In the second reaction stage in the process according to the invention, the imido-ester hydrochlorides obtained in the first stage are reacted with cyanamide in the aqueous phase, during which a pH value of 5-8, preferably 5-6.2, is established with the addition of bases. Only in this way is it possible to prepare N-cyanimido-esters with high yields and good purities. The pH value can be established at the start of the reaction with the usual alkaline substances, such as sodium hydroxide solution or potassium hydroxide solution, and also with sodium carbonate or potassium carbonate and with aqueous ammonia solution. After the reaction has started, further pH correction is no longer necessary.

The cyanamide, which is added to the imido-ester hydrochlorides either in stoichiometric amounts or in a small excess, preferably is used in the form of a technical grade 50% strength solution.

The second reaction stage should be carried out at temperatures between $-10°$ and $+50°$ C., but temperatures between $0°$ and $+18°$ C. preferably are maintained, such as by using water or a cooling brine as a coolant.

At these stated temperatures, the reaction proceeds relatively rapidly after the pH value has been established at the start of the reaction, and usually ends after a period of 30 to 90 minutes. As in the first stage, the reaction can be carried out batchwise, semicontinuously, such as, for example, in a cascade of stirred kettles, or continuously.

The N-cyanimido-esters can be isolated by simply separating off the organic phase from the aqueous phase or by solvent extraction, in which case methylene chloride has proved to be a particularly suitable extraction agent. It is also possible to combine the two methods.

In the preparation of the cyanimido-esters, according to the present invention, the crude yield from the second process stage is about 92-98%, the purity of this product being about 96-99%. Although the yield and purity of the cyanimido-esters depend on the quality of the imido-ester hydrochloride employed, a very pure starting substance is not absolutely necessary in the second stage. Thus, for example, an undried product moistened with ethyl acetate from the first stage can be used. It is thereby possible to carry out the two stages in a type of "one-pot reaction" by a procedure in which, when the first reaction stage has ended, the acetic acid ester is evaporated off and the second stage is then carried out in the same reaction vessel.

Because of their high purity, the N-cyanimido-esters obtained as the crude product usually are suitable for further reactions without prior purification by distillation. However, if necessary, the crude product can be dried in the customary manner, for example, using anhydrous sodium sulfate or molecular sieves.

In the third reaction stage, the N-cyanimido-esters of the general formula:

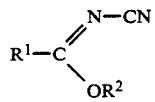

where $R^1$ is selected from the group consisting of H, alkyl with 1 to 24 carbon atoms, aralkyl, such as, for example, benzyl, or aryl, such as, for example, phenyl, and $R^2$ is selected from the group consisting of alkyl with 1 to 4 carbon atoms, are reacted with a compound selected from the group consisting of salts of O-alkylisoureas, S-alkylisothioureas, guanidines and amidines.

O-Methyl- and O-ethyl-isourea salts have proved to be particularly advantageous as the O-alkylisourea salt, whilst S-methylisothiourea salts are particularly preferred in the case of the S-alkylisothiourea salts.

Amidine derivatives which can be used are both compounds with aliphatic substitutents, such as methyl, ethyl, propyl and butyl, and those with aromatic or araliphatic radicals, such as phenyl or benzyl.

In the case of guanidine salts, the unsubstituted or monosubstituted guanidines or guanidines disubstituted on one nitrogen atom are preferred, suitable substitutents being, in particular, alkyl or aryl radicals.

In principle, all inorganic or organic salts can be employed as salts of the O-alkylisourea, S-alkylisourea, amidine or guanidine derivatives. Particularly suitable organic salts are acetates and particularly suitable inorganic salts are sulfates, bisulfates, hydrochlorides and bicarbonates, because these are most readily available industrially.

The reaction of N-cyanimido-esters with these salts in the third stage must proceed in the presence of basic reagents, and the customary reagents, such as sodium methylate and alkali metal hydroxides, such as sodium hydroxide and potassium hydroxide, can be selected depending on the solvent used. However, it is also possible to deviate to other bases, such as, for example, sodium carbonate or potassium carbonate, without problems, if this should be advantageous for any reasons.

The third stage reaction is preferably carried out in an alcoholic, aqueous or aqueous-alcoholic phase. Possible solvents are thus, above all, water, methanol, ethanol, n-propanol or i-propanol and mixtures thereof.

As a rule, it is sufficient to employ the three reaction components, i.e., the N-cyanimido-ester, the salt and the base, in stoichiometric or approximately stoichiometric amounts. However, if the reactions should proceed less smoothly, it is advisable to use the N-cyanimido-ester in excess.

According to the present invention, the salt preferably is present in the particular solvent, and the base and the N-cyanimido-ester are then added thereto in succession. However, it is also possible to introduce the base into a mixture of the N-cyanimido-ester and the salt.

The reaction temperatures can be varied within the temperature range of about $-10°$ to $+50°$ C. The preferred temperatures range between $0°$ and $+40°$ C.

In a particularly preferred embodiment for the preparation of 2-amino-4-methoxy-6-alkyl-s-triazines, the O-methylisourea sulfate, which can also be employed in a mixture with O-methylisourea bisulfate, is first introduced into a methanolic sodium methylate solution which has been cooled to $0°-12°$ C., and the corresponding N-cyanimido-ester is then added at a rate such that the internal temperature does not rise above $20°$ C. Thereafter, the cyclization reaction is brought to completion at about $20°$ to $40°$ C.

The reaction mixture is worked up by customary methods, such as cooling or concentrating the solution and separating off the resulting solid by filtration or centrifugation.

If the reaction is carried out in a purely alcoholic solution, it has proved particularly advantageous to add water to the reaction mixture before it is worked up, 100 to 200 ml of water preferably being used per liter of alcoholic solvent. In this manner, optimum filterability or centrifugability of the alcoholic reaction mixture is achieved, without the yield or product quality being reduced. This water can also be added during the after-reaction.

The product separated off, which is obtained in yields of up to 99% and has a purity of up to 99%, can also be dried, if appropriate, by customary method.

The process according to the invention is mainly characterized by the high yields and degrees of purity over all three stages, and by the simple industrial process steps and the inexpensive chemicals used, so that this process can be carried out on a large industrial scale without problems.

The following Examples 1 to 19, which describe the preparation of the imido-ester hydrochlorides (1st stage: Examples 1–3), the N-cyanimido-esters (2nd stage: Examples 4–8) and the 2-amino-s-triazines (3rd stage: Examples 9–19) are intended to illustrate the invention in more detail, but without limiting it thereto.

EXAMPLE 1

319 g (8.75 moles) of gaseous hydrogen chloride were passed into a mixture of 332 g (8 moles) of 99% pure acetonitrile and 372 g (8 moles) of technically absolute ethanol (99% pure), while stirring and cooling externally with cold water and with the exclusion of atmospheric moisture, over a period of 2 hours in a manner such that the internal temperature did not rise above 25° C. The mixture was then stirred for a further 3 hours, with cooling to a temperature of about 12° C. The internal temperature was then allowed to rise slowly to 30° C. The mixture was stirred for a further 2 hours at 30° C. (gentle cooling) and 265 g of ethyl acetate were then added. After addition of the ethyl acetate, the reaction mixture was stirred overnight at room temperature (internal temperature about 25° C.) for 18 hours. A further 180 g of ethyl acetate were than added and stirring was continued at room temperature for 6 hours. After cooling to 12° C., the mixture was filtered with suction and the solid residue was dried in a vacuum drying cabinet at 50° C. (20 mbar). The yield was 937 g (94.8% of theory) of acetimido-ethyl ester hydrochloride having a melting point of 107° C. (decomposition) (Literature: A. Pinner, Die Imidoather und ihre Derivate (The imidoethers and their derivatives) (Berlin 1892), page 27: 98°–100° C. (decomposition)).

$C_4H_{10}ClNO$ (123.58): Calculated N 11.33; Found N 11.62; Calculated Cl 28.69; Found Cl 28.50.

EXAMPLE 2

885 g of technically pure ethyl acetate, 745 g (16 moles) of technically absolute ethanol (99% pure, denatured with 1% of petroleum ether) and 664 g (16 moles) of 99% pure acetonitrile were mixed and 622 g (17.06 moles) of gaseous, anhydrous hydrogen chloride were introduced, while stirring and cooling externally with cold water, over a period of 4 hours (with exclusion of atmospheric moisture) such that the internal temperature did not rise above 20° C. The reaction mixture was then stirred at an internal temperature of 20°-22° C. for 72 hours. After cooling to 12° C., the solid reaction product was filtered off with suction and dried in a vacuum drying cabinet at 50° C. under the vacuum of a waterpump. The yield was 1,872 g (94.7% of theory) of acetimido-ethyl ester hydrochloride having a melting point of 111° C. (decomposition).

EXAMPLE 3

(a) Batch 1

292 g (8 moles) of gaseous hydrogen chloride were passed into a mixture of 332 g (8 moles) of acetonitrile (99% pure), 373 g (8 moles) of technically absolute ethanol (99% pure, denatured with 1% of petroleum ether) and 443 g of technically pure ethyl acetate (acetic acid ethyl ester), while stirring and cooling externally with cold water and with exclusion of atmospheric moisture, over a period of 2.5 hours so that the internal temperature did not rise above 20° C.

The mixture was then stirred at an internal temperature of 20°-25° C. for a further 22 hours. It was then cooled to about 12° C. and filtered with suction and the solid was dried in a vacuum drying cabinet at 50° C. under a waterpump vacuum. The yield was 794 g (80.3% of theory) of acetimido-ethyl ester hydrochloride having a melting point of 109° C. (decomposition), 498 g of filtrate being obtained.

$C_4H_{10}ClNO$ (123.58): Calculated Cl 28.69; Found Cl 28.70.

(b) Batch 2

498 g of the filtrate from batch 1, 332 g (8 moles) of acetonitrile (99% pure), 373 g (8 moles) of technically absolute ethanol and 80 g of ethyl acetate were mixed and 292 g (8 moles) of gaseous hydrogen chloride were passed into this solution, while stirring and cooling externally with cold water, over a period of 2.5 hours (with exclusion of atmospheric moisture) so that the internal temperature did not rise above 20° C.

The reaction mixture was then stirred at an internal temperature of 20°-25° C. for a further 22 hours and cooled to 12° C. and the solid reaction product was isolated by filtration with suction.
Amount weighed: 924 g (93.5%) of acetimido-ethyl ester hydrochloride having a melting point of 108° C. decomposition).
Calculated Cl 28.69; Found Cl 29.40.
Filtrate: 481 g.

(c) Batch 3

The procedure followed was similar to batch 2, using: 481 g of filtrate from batch 2, 332 g (8 moles) of acetonitrile, 99% pure, 373 g (8 moles) of ethanol, technically absolute, 99% pure, 200 g of ethyl acetate, technically pure, and 292 g (8 moles) of hydrogen chloride.

The yield was 928 g (93.8%) of acetimido-ethyl ester hydrochloride having a melting point of 108° C. (decomposition), 623 g of filtrate being obtained.

Calculated N 11.33; Found N 11.94; Calculated Cl 28.69; Found Cl 29.40.

(d) Batch 4

The procedure followed was similar to batch 2, using: 623 g of filtrate from batch 3, 332 g (8 moles) of acetonitrile, 99% pure, 373 g (8 moles) of ethanol, technically absolute, 99% pure, and 292 g (8 moles) of hydrogen chloride.

935 g (94.6%) of acetimido-ethyl ester hydrochloride having a melting point of 105° C. (decomposition) and 567 g of filtrate were obtained.

Calculated Cl 28.69; Found Cl 29.10 %.

(e) Batch 5

567 g of filtrate from batch 4, 332 g (8 moles) of acetonitrile, 99% pure, 373 g (8 moles) of ethanol, technically absolute, 99% pure, and 292 g (8 moles) of hydrogen chloride.

The procedure followed was similar to batch 2, 1,012 g (102.3%) of acetimido-ethyl ester hydrochloride having a melting point of 108° C. (decomposition) and 447 g of filtrate resulting.

Calculated N 11.33; Found N 12.11; Calculated Cl 28.69; Found Cl 29.10.

(f) Batch 6

447 g of filtrate from batch 5, 332 g (8 moles) of acetonitrile, 99% pure, 373 g (8 moles) of ethanol, technically absolute, 99% pure, and 292 g (8 moles) of hydrogen chloride.

The procedure followed was similar to batch 2, but the reaction product filtered off with suction was not dried.

The yield was 983 g (93.8%) of acetimido-ethyl ester hydrochloride with a solvent content (degree of moisture) of 5.6%. 385 g of filtrate were obtained.

After drying in vacuo at 50° C., the product had a melting point of 109° C. (decomposition):
Calculated N 11.33; Found N 12.07; Calculated Cl 28.69; Found Cl 29.20.

OVERALL BALANCE OF BATCHES 1-6

| Starting substances: | Acetonitrile (99% pure) | 1,992 g |
|---|---|---|
| | Ethanol (technically absolute) | 2,239 g |
| | Ethyl acetate | 723 g |
| | Hydrogen chloride (anhydrous) | 1,752 g |
| Yield: | 5,521 g (93%) of acetimido-ethyl ester hydrochloride | |
| Filtrate (waste): | 385 g | |

EXAMPLE 4

101 g (1.2 moles of cyanamide) of 50% strength aqueous cyanamide solution (SKW-cyanamide L 500) were added to 200 Ml of cold water, and 131 g (1 mole) of ethyl acetate-moist acetimido-ethyl ester hydrochloride from the preceding Example 3/Batch 6 with a solids content of 94% (melting point of the dried product: 109° C. (decomposition) were introduced, while stirring and cooling externally with cold water. When the addition of the acetimido-ethyl ester hydrochloride had ended (pH=1.7), a pH value of 6.15 (calibrated glass electrode) was established by addition of 2.84 g (0.036 mole) of 50% strength sodium hydroxide solution, during which the internal temperature rose from 11° to 16° C.

The reaction mixture was then stirred for a further 90 minutes, while cooling externally with cold water, and the reaction mixture was extracted twice with 200 ml of methylene chloride each time. The organic phase was dried over anhydrous sodium sulfate. After the methylene chloride had been stripped off on a rotary evaporator, 108,5 g (96.8% of theory) of N-cyanoacetimido-ethyl ester with a degree of purity of 99.3%, determined by gas chromatography, were obtained.

EXAMPLE 5

494 g (4.0 moles) of dried acetimido-ethyl ester hydrochloride having a melting point of 107° C. (decomposition) were introduced into a mixture, cooled to 11° C. (=cooling water temperature), of 404 g (4.8 moles) of 50% aqueous cyanamide solution (SKW-cyanamide L 500) and 800 ml of water, while stirring, during which the internal temperature fell to 8° C. and the pH value was 2.3. A pH value of 6.0 was then established (11° C., glass electrode) by addition of 50% sodium hydroxide solution (about 7.2 g=0.09 mole), and the reaction mixture was stirred for a further 60 minutes, while cooling externally with cold water. (After stirring for 10 minutes, the pH value had risen to 6.5 and the internal temperature had risen to 16° C. After stirring for 20 minutes, the pH value was 6.9 and the internal temperature was 13° C.).

The reaction mixture (pH=6.3; internal temperature=12° C.) was then introduced into a separating funnel and the organic (lighter) phase was separated off. The amount weighed was 418 g (93.2% of theory) of moist N-cyanoacetimido-ethyl ester with a content of 97.2% (according to the gas chromatogram). It was possible to obtain an additional 17 g (3.8%) of crude product by extraction of the aqueous phase with methylene chloride.

EXAMPLE 6

400 ml of water and 202 g (2.4 moles of cyanamide) of technical grade 50% aqueous cyanamide solution were mixed and cooled to 0° C. by external cooling with a cooling brine. 247 g (2 moles) of dried acetimido-ethyl ester hydrochloride having a melting point of 106° C. (decomposition) were then added, while stirring, and the pH value was increased from 2.3 to pH 6 (0° C.) by the addition of 2.4 g of 50% sodium hydroxide solution. The mixture was then subsequently stirred at an internal temperature of −1° to +1° C. for a further 3 hours. Thereafter, the reaction mixture was extracted twice with 200 ml of methylene chloride each time. The undried organic phase was concentrated under a waterpump vacuum (until an internal temperature of 60° C. was reached), 218 g (97.2% of theory) of N-cyanoacetimido-ethyl ester of 97.9% purity (according to analysis by gas chromatography) remaining:

$C_5H_8N_2O$ (112.12): Calculated N 24.99; Found N 24.84.

The crude N-cyanoacetimido-ethyl ester was then distilled, a 99.9% pure product (determination by gas chromatography) having a boiling point of 86°–88° C./9 mm Hg (W Lwowski, Synthesis 1971, 263=102/17 mm) being obtained in a yield of 97.7%:

Calculated N 24.99; Found N 25.09.

EXAMPLE 7

61.8 g (0.5 mole) of acetimido-ethyl ester hydrochloride were added to 42.1 g (0.5 mole) of 50% aqueous cyanamide solution, while stirring and cooling externally with cold water, and a pH value of 5 was established (13° C.) with concentrated aqueous ammonia solution. The mixture was then stirred for a further hour, while cooling, during which the pH value initially rose to 7.3 and then dropped to 6.9. 120 ml of water were added to the reaction mixture in order to dissolve the ammonium chloride which had precipitated. The mixture was extracted twice with 100 ml of methylene chloride each time.

The organic phase was dried over anhydrous sodium sulfate. After the methylene chloride had been stripped off in a rotary evaporator, 51.6 g (92% of theory) of N-cyanoacetimido-ethyl ester with a purity of 99.3%, determined by gas chromatography, remained.

EXAMPLE 8 (COMPARISON)

400 ml of water and 202 g (2.4 moles of cyanamide) of 50% aqueous cyanamide solution (SKW-cyanamide L 500) were mixed and cooled to 11° C. 247 g (2 moles) of dried acetimido-ethyl ester hydrochloride having a melting point of 104° C. (decomposition) were introduced, while stirring and cooling externally with cold water, and the pH value was increased from 3.2 to 4.1 (11° C.) by addition of 0.2 g of 50% strength sodium hydroxide solution. Thereafter, the mixture was stirred for a further 2.5 hours, while cooling with water, during which the pH value dropped again to pH 2.6 (11° C.). The reaction mixture was extracted by shaking with 300 ml of methylene chloride and the organic phase was separated off with the aid of a separating funnel. After the methylene chloride had been stripped off in a rotary evaporator under the vacauum of a waterpump at a bath temperature of 60° C., the yield was 27 g (12% of theory) of product.

EXAMPLE 9

A mixture of 448.4 g (2.49 moles of sodium methylate) of 30% methanolic sodium methylate solution (technical grade product from BASF AG) and 675 ml of methanol was cooled to −10° C. (cooling brine).

307.8 g (corresponding to 2.4 moles of O-methylisourea) of technical grade O-methylisourea sulfate (O-methylisourea sulfate content: 92.5%, O-methylisourea bisulfate content: 4.9%, O-methylisourea content: 96% of theory) from SKW Trostberg AG were then introduced, while stirring and with the exclusion of atmospheric moisture, and stirring was continued for a further 15 minutes. 281 g (2.49 moles) of crude N-cyanoacetimido-ethyl ester (content: 99.3%) were then added dropwise, while stirring and cooling externally, in a manner such that the internal temperature did not rise above −8° C. The reaction mixture was then stirred at −10° C. for a further 24 hours, 100 ml of water were subsequently added and the solid residue (mixture of 2-amino-4-methoxy-6-methyl-s-triazine and sodium sulfate) was filtered off with suction. To remove the sodium sulfate, the solid residue was stirred twice in 1,000 ml of water each time (about 30 minutes) and then washed free from sodium sulfate with 300 ml of water on a suction filter. After drying in a vacuum drying cabinet at 80° C. (about 20 mbar), the yield was 321 g (95.4%) of colorless 2-amino-4-methoxy-6-methyl-s-triazine having a melting point of 262°–264° C. (decomposition).

EXAMPLE 10

A mixture of 1,441 g (8 moles) of 30% technical grade methanolic sodium methylate solution (BASF AG) and 2,150 ml of methanol was cooled to 0° C.

984.8 g (4 moles) of pure O-methylisourea sulfate (O-methylisourea sulfate, pure from SKW Trostberg AG) were added to this cooled solution, while stirring vigorously and with exclusion of atmospheric moisture, and the mixture was cooled at 0° C. for a further 15 minutes. 897 g (8 moles) of pure N-cyanoacetimido-ethyl ester were then added dropwise, while stirring and cooling externally (ice bath), such that the internal temperature did not rise above 6° C. When the addition of the N-cyanoacetimido-ethyl ester had ended, the mixture was stirred at an internal temperature of 0° C. for a further 2 hours. Thereafter, the reaction mixture was stirred at room temperature, without external cooling, for 22 hours and then cooled to 12° C. and centrifuged. To remove the sodium sulfate, the solid residue was suspended in 4 liters of water and the suspension was centrifuged.

The residue was suspended once again in 4 liters of water, the suspension was centrifuged and the centrifugate was washed free of sodium sulfate. It was dried at 80° C. in a vacuum drying cabinet. The yield was 1,095 g (97.7%) of 2-amino-4-methoxy-6-methyl-s-triazine having a melting point of 262°–264° C. (decomposition).

EXAMPLE 11

900 g (5 moles) of 30% methanolic sodium methylate solution (technical grade) and 1,350 ml of methanol were taken together, with exclusion of atmospheric moisture, and 617 g (2.5 moles) of O-methylisourea sulfate, pure from SKW Trostberg AG (corresponding to 5 moles of O-methylisourea) were introduced, while stirring and cooling externally with cold water, and stirring was continued for a further 15 minutes. 577 g (5 moles) of crude N-cyanoacetimido-ethyl ester with a content of 97.9% were added dropwise, while stirring vigorously and cooling externally by running cold water, at a rate such that the internal temperature did not rise above 20° C.

When the addition of the N-cyanoacetimido-ethyl ester had ended, the mixture was stirred for a further 2 hours, while cooling externally with cold water. The reaction mixture was then stirred for 17 hours, without cooling (room temperature: about 20° C.), 200 ml of water were subsequently added and stirring was continued at room temperature for a further 25 hours. The mixture was filtered with suction and the colorless residue was suspended twice in 2,000 ml of water each time, to remove the sodium sulfate, and then washed free from sodium sulfate on a suction filter. After drying in a vacuum drying cabinet at 80° C. (20 mbar), 694 g (99% of theory) of 2-amino-4-methoxy-6-methyl-s-triazine having a melting point of 262° C. (decomposition) were obtained.

EXAMPLE 12

A solution of 404 g (10 moles) of sodium hydroxide (99% pure) in 2,500 ml of water was cooled to +3° C. and 931 g (5 moles) of O-ethylisourea bisulfate were introduced, while stirring and cooling externally (ice bath), at a rate such that the internal temperature did not rise above +10° C. 561 g (5 moles) of pure N-cyanoacetimido-ethyl ester were added dropwise in the course of two hours, while stirring vigorously, such that the internal temperature did not rise above +6° C., a further 500 ml of cold water being added after addition of 280 g of the N-cyanoacetimido-ethyl ester (for better stirrability). When the addition of the N-cyanoacetimido-ethyl ester had ended, the mixture was stirred in an ice bath for a further 2 hours. The reaction mixture was then brought to +13° C. and stirred at this temperature (cooling with cold water) for 17 hours. The mixture was warmed to +40° C. and stirred at this temperature for a further 2 hours. After cooling to +15° C., the solid residue was filtered off with suction, suspended twice in 1,500 ml of cold water each time and then rinsed with 300 ml of water on a suction filter. After drying in a vacuum drying cabinet at 50° C. (under the vacuum of a waterpump), 359 g (46.6% of theory) of 2-amino-4-ethoxy-6-methyl-s-triazine having a melting point of 175°–177° C. were obtained (Literature: 173°–175° C., French Pat. No. 1,380,818).

Note: The literature yield via guanyl-O-ethyl-isourea hydrochloride is 22.6% (French Pat. No. 1,380,818).

EXAMPLE 13

A mixture of 1,080 g (6 moles of 30% methanolic sodium methylate solution (technical grade, BASF AG) and 1,600 ml of methanol was prepared, with exclusion of atmospheric moisture, and 739 g (3 moles) of O-methylisourea sulfate (100% pure product from SKW Trostberg AG, corresponding to 6 moles of O-methylisourea) were added, while stirring vigorously and cooling externally (cooling brine), to the sodium methylate solution, which had been cooled to 0° C. for a further 15 minutes and 757 g (6 moles) of N-cyanopropioimido-ethyl ester (=N-cyanopropionic acid imido-ethyl ester) were then added dropwise, while stirring intensively and with exclusion of atmospheric moisture, such that the internal temperature did not rise above 5° C. When the addition of the N-cyanopropioimido-ethyl ester had ended, the mixture was stirred at an internal temperature of 0° C. for a further 2 hours. Thereafter, the reaction mixture was stirred for 40 hours, without external cooling (room temperature: about 20° C.), and was then warmed to 40° C. and stirred at this temperature for a further 2 hours. It was cooled to 15° C., 300 ml of water were added (for better filterability) and the solid residue was then filtered off with suction. The filtrate was concentrated to dryness in a rotary evaporator. The solid residues were combined and, to remove the sodium sulfate, were suspended twice in 4 liters of water each time, while stirring vigorously. Thereafter, the residue was rinsed again with 1 liter of water on a suction filter and dried in a vacuum drying cabinet at 80° C.

The yield was 792 g (85.6% of theory) of 2-amino-4-ethyl-6-methoxy-s-triazine having a melting point of 152°–154° C. (Literature: 150°–151° C., French Pat. No. 1,380,818).

The literature yield via guanyl-O-methylisourea hydrochloride is 29.8% of theory (French Pat. No. 1,380,818).

EXAMPLE 14

The procedure followed was analogous to Example 13, using N-cyanobutyrimido-ethyl ester (=N-cyano-n-butyric acid imido-ethyl ester), and 730 g (72.3% of theory) of 2-amino-4-methoxy-6-n-propyl-s-triazine having a melting point of 111°–113° C. were obtained (Literature: 111°–111.5° C., French Pat. No. 1,380,818).

The literature yield via guanyl-O-methylisourea hydrochloride is 19% of theory (French Pat. No. 1,380,818).

EXAMPLE 15

The procedure followed was analogous to Example 13, using N-cyanoisobutyrimido-ethyl ester (=N-cyano-isobutyric acid imido-ethyl ester). 739 g (73.2%)

of 2-amino-4-isopropyl-6-methoxy-s-triazine with a melting point of 116°–118° C. were obtained here.

$C_7H_{12}N_4O$ (168.2): Calculated C 49.99; Found C 49.78; Calculated H 7.19; Found H 7.09; Calculated N 33.31; Found N 33.14.

EXAMPLE 16

The procedure followed was analogous to Example 13, using N-cyanolauric acid imido-ethyl ester (dissolved in 500 ml of methanol), and 1,617 g (96.1%) of 2-amino-4-methoxy-6-n-undecyl-s-triazine having a melting point of 86°–88° C. were obtained.

$C_{15}H_{28}N_4O$ (280.41): Calculated C 64.25; Found C 63,87; Calculated H 10.06; Found H 10.15; Calculated N 19.98; Found N 19.71.

EXAMPLE 17

100.5 g (0.432 mole) of 4-chlorophenylguanidine nitrate were added to a cold mixture, at 0° C., of 77.8 g (0.432 mole) of a 30% methanolic solution of sodium methylate and 200 ml of methanol, while stirring and with exclusion of atmospheric moisture, and the mixture was subsequently stirred for 15 minutes. 48.5 g (0.432 mole) of pure N-cyanoacetimido-ethyl ester were added dropwise, while stirring and cooling externally (with an ice bath), in a manner such that the internal temperature did not rise above 5° C. The reaction mixture was stirred for a further 4 hours, while cooling with ice, and then brought to room temperature (20° C.) and stirred for 60 hours without external cooling. The solid residue was then filtered off with suction and, to remove the sodium nitrate, suspended twice in 500 ml of water each time, while stirring, and then rinsed with 500 ml of water on a suction filter. After drying in a vacuum drying cabinet at 80° C., the yield was 100.6 g (98.8%) of 2-amino-4-(4-chlorophenylamino)-6-methyl-s-triazine having a melting point of 226° C. (decomposition).

$C_{10}H_{10}ClN_5$ (235.68): Calculated C 50.96; Found C 50.73; Calculated H 4.28; Found H 4.24; Calculated N 29.72; Found N 29.68.

EXAMPLE 18

278 g (1 mole) of S-methylisothiourea sulfate (corresponding to 2 moles of S-methylisourea) were added to a mixture of 360 g (2 moles) of 30% methanolic sodium methylate solution and 600 ml of methanol at 0° C., while stirring and with exclusion of moisture. The mixture was subsequently stirred for a further 15 minutes. 224 g (2 moles) of pure N-cyanoacetimido-ethyl ester were then added dropwise, while stirring and cooling externally (cooling brine), such that the internal temperature did not exceed 5° C. The mixture was first stirred at 0°–1° C. for 5 hours and then brought to the ambient temperature and stirred for a further 64 hours without external cooling. The precipitate was filtered off with suction and the filtrate was concentrated to dryness in a rotary evaporator. The two solid residues were combined and, to remove the sodium sulfate, were suspended in 800 ml of water, with stirring. The suspension was filtered with suction and the residue was suspended once again in 800 ml of water. It was filtered off with suction again and rinsed with 500 ml of water on a suction filter. After drying in vacuo at 80° C., 250 g of 2-amino-4-methyl-6-methylmercapto-s-triazine having a melting point of 161°–163° C. were obtained.

$C_5H_8N_4S$ (156.21): Calculated C 38.44; Found C 38.07; Calculated H 5.16; Found H 5.12; Calculated N 35.87; Found N 35.69; Calculated S 20.53; Found S 20.34.

EXAMPLE 19

The procedure followed was analogous to Example 18, using 1 mole of N, N-dimethylguanidine sulfate (2:1), and 276 g (90.1%) of 2-amino-4-dimethylamino-6-methyl-s-triazine having a melting point of 194°–196° C. were obtained.

$C_6H_{11}N_5$ (153.19): Calculated C 47.04; Found C 47.13; Calculated H 7.24; Found H 7.18; Calculated N 45.72; Found N 45.28.

EXAMPLE 20

The procedure followed was analogous to Example 18, using 1 mole of N, N-diethylguanidine sulfate (2:1). 322 g (88.8%) of 2-amino-4-diethylamino-6-methyl-s-triazine having a melting point of 125°–127° C. resulted here.

$C_8H_{15}N_5$ (181.24): Calculated C 53.02; Found C 52.72; Calculated H 8.34; Found H 8.40; Calculated N 38.64; Found N 38.50.

EXAMPLE 21

The procedure followed was analogous to Example 18, using 2 moles of benzamidine hydrochloride, and 337 g (90.5% of theory) of 2-amino-4-methyl-6-phenyl-s-triazine having a melting point of 154°–158° C. were obtained (Literature: 156.5°–158° C., K. R. Huffmann and F. C. Schaefer, J. Org. Chem. 28, 1816 (1963)).

Variations and modifications of the present invention will be apparent to those skilled in the art within the scope of the present claims.

Having thus described the invention, what is claimed is:

1. A process for the preparation of a 2-amino-s-triazine in high yield and high purity comprising the steps of mixing together in an aqueous, alcoholic or aqueous-alcoholic reaction medium approximately stoichiometric amounts of reaction components comprising (a) an N-cyanimido ester having the formula:

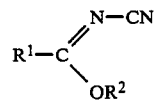

in which R1 is selected from the group consisting of hydrogen, akyl having from 1 to 24 carbon atoms, aralkyl and aryl, and R2 is an alkyl group having 1 to 4 carbon atoms; (b) a salt compound selected from the group consisting of salts of O-alkyl isoureas, s-alkyl isothioureas, guanidines and amidines, and (c) a base selected from the group consisting of sodium methylate, sodium carbonate, potassium carbonate and alkali metal hydroxides, reacting said reaction components at a temperature of between −10° C. and 50° C. for a sufficient period of time to form a reaction product comprising said 2-amino-s-triazine, and washing and drying said reaction product to form said 2-amino-s-triazine in high yield and high purity.

2. A process for the preparation of 2-amino-4-methoxy-6-methyl-s-triazine according to claim 1 in a yield of about 95% in which the reaction components are (a) N-cyanoacetimido-ethyl ester; (b) O-methylisourea sulfate and (c) sodium methylate.

3. A continuous process according to claim 1 in which said N-cyanimido ester is formed in high yield by reacting an imido ester hydrochloride with cyanamide in an aqueous phase which has been brought to a pH value of 5-8 by the addition of a base, and at a temperature between −10° C. and 50° C.

4. A continuous process according to claim 3 in which said imido ester hydrochloride is formed in high yield in a first stage by reacting a nitrile, an alcohol and hydrogen chloride in the presence of an acetic ester at a temperature between −10° C. and 45° C. to form a reaction product comprising said imido ester hydrochloride.

5. The process of claim 4 wherein 0.3-2 moles, preferably 0.5-1 mole, of acetic acid ester per mole of nitrile is used in the first stage.

6. The process of claim 4 wherein 0.3-2 moles, preferably 0.5-1 mole, of acetic acid ester per mole of alcohol are used in the first stage.

7. The process of claim 4 wherein the temperature in the first reaction stage is 10° to 30° C.

8. The process of claim 4 wherein, in the first stage, the hydrogen chloride is passed into a mixture of the nitrile and the alcohol, and the acetic acid ester is added gradually as the reaction mixture becomes more difficult to stir.

9. The process of claim 4 wherein the reaction product of the first stage is filtered or centrifuged and the mother filtrate or centrifugate of the first stage is reused as the diluent and/or reaction medium for the first stage of a repeat of the process.

10. The process of claim 3 wherein said reaction is carried out at a pH value of 5-6.2.

11. The process of claim 3 wherein the cyanamide is used in the form of a technical grade 50% aqueous solution.

12. The process of claim 3 wherein said reaction is carried out at a temperature of 0° to +18° C.

13. The process of claim 3 wherein the reaction time is 30 to 90 minutes.

14. The process of claim 3 wherein the N-cyanimido-ester is isolated by solvent extraction.

15. The process of claim 14 wherein methylene chloride is used as the extraction agent.

16. The process of claim 1 wherein an O-alkylisourea salt is used, selected from the group consisting of O-methyl- and O-ethyl-isourea salts as the O-alkylisourea salt.

17. The process of claim 1 wherein an S-methylisothiourea salt is used as the S-alkylisothiourea salt.

18. The process of claim 1 wherein the salt used is selected from the group consisting of sulfates and bisulfates.

19. The process of claim 1 wherein sodium methylate is used as the base.

20. The process of claim 1 wherein sodium hydroxide or potassium hydroxide is used as the base.

21. The process of claim 1 wherein the reaction is carried out in alcoholic solution.

22. The process of claim 1 wherein the reaction is carried out in the aqueous phase.

23. The process of claim 1 wherein the salt is present in an appropriate solvent, and the base and N-cyanimido-ester are added thereto in succession.

24. The process of claim 1 wherein the base is introduced into a mixture of the N-cyanimido-ester and the salt.

25. The process of claim 1 wherein the reaction temperature is 0° to +40° C.

26. The process of preparing a 2-amino-4-methoxy-6-alkyl-s-triazine according to claim 1 which comprises adding O-methylisourea sulfate to a methanolic sodium methylate solution, which has been cooled to 0°-12° C., adding N-cyanimido-ester at a rate such that the internal temperature does not rise above 20° C., and thereafter completing the cyclization reaction at a temperature of about 20° to 40° C.

27. The process of claim 26 wherein, in the third stage, water is added to the reaction mixture for preparing the alcoholic reaction solution.

28. The process of claim 27 wherein 100 to 200 ml of water per liter of alcoholic solvent are added to the reaction mixture.

* * * * *

UNITED STATES PATENT AND TRADEMARK OFFICE
CERTIFICATE OF CORRECTION

PATENT NO. : 4,587,337
DATED : May 6, 1986
INVENTOR(S) : Stefan Weiss et al.

It is certified that error appears in the above-identified patent and that said Letters Patent is hereby corrected as shown below:

On the title page,
    Other Publications -  "and the" should be -- und ihre --.

Column 2, line 1, "in", second occurrence, should be -- is --

Claim 27, lines 1 and 2, delete  ", in the third stage,".

Signed and Sealed this

Fifth Day of August 1986

[SEAL]

Attest:

DONALD J. QUIGG

Attesting Officer

Commissioner of Patents and Trademarks